(12) United States Patent
Lee et al.

(10) Patent No.: US 8,967,218 B2
(45) Date of Patent: Mar. 3, 2015

(54) ALGINATE-CONTAINING WOUND DRESSING, METHOD AND APPARATUS FOR MAKING THE SAME

(71) Applicant: Taiwan Textile Research Institute, Tu-Chen, Taipei Hsien (TW)

(72) Inventors: Jui-Sheng Lee, Tu-Chen (TW); Chan-Yi Yang, Tu-Chen (TW)

(73) Assignee: Taiwan Textile Research Institute, New Taipei (TW)

( * ) Notice: Subject to any disclaimer, the term of this patent is extended or adjusted under 35 U.S.C. 154(b) by 255 days.

(21) Appl. No.: 13/792,463

(22) Filed: Mar. 11, 2013

(65) Prior Publication Data
US 2013/0186555 A1    Jul. 25, 2013

Related U.S. Application Data

(62) Division of application No. 12/648,107, filed on Dec. 28, 2009, now Pat. No. 8,413,702.

(30) Foreign Application Priority Data

Jul. 28, 2009    (TW) ............................... 98125403 A

(51) Int. Cl.
*A61F 13/00*    (2006.01)
*B32B 5/12*    (2006.01)
(Continued)

(52) U.S. Cl.
CPC ..... *A61F 13/00029* (2013.01); *A61F 13/00012* (2013.01); *A61F 13/00038* (2013.01); *A61F 13/00995* (2013.01); *A61F 2013/00229* (2013.01); *A61F 2013/00238* (2013.01); *A61F 2013/00544* (2013.01); *B29C 53/66* (2013.01); *B29C 53/8016* (2013.01); *B29C 2053/8025* (2013.01)

USPC .......................................................... 156/425

(58) Field of Classification Search
None
See application file for complete search history.

(56) References Cited

U.S. PATENT DOCUMENTS

| 4,943,334 A | 7/1990 | Medney et al. |
| 5,714,232 A * | 2/1998 | Fenton et al. ................. 428/171 |
| 2008/0000406 A1 | 1/2008 | Couto |

(Continued)

FOREIGN PATENT DOCUMENTS

| CN | 1342800 A | 4/2002 |
| CN | 101096801 A | 1/2008 |

(Continued)

OTHER PUBLICATIONS

English translation of abstract of CN 1342800 A (published Apr. 3, 2002).

(Continued)

*Primary Examiner* — Michael B Pallay
(74) *Attorney, Agent, or Firm* — McClure, Qualey & Rodack, LLP

(57) ABSTRACT

Disclosed herein is a method for manufacturing a wound dressing. The method includes the steps of: forming a alginate fiber by a wet spinning process; winding the alginate fiber around a board to form a plurality of first fibers on a surface of the board; spraying an aqueous solution containing sodium ions on the surface of the wound first fiber; rewinding the alginate fiber around the board to form a plurality of second fibers stacked on the first fibers, in which the second fibers are not parallel with the first fibers; and drying the first fibers and the second fibers.

5 Claims, 14 Drawing Sheets

(51) Int. Cl.
*B29C 53/66* (2006.01)
*B29C 53/80* (2006.01)

(56) References Cited

U.S. PATENT DOCUMENTS

2009/0138082 A1 5/2009 Reah et al.
2010/0137772 A1 6/2010 Tanaka et al.

FOREIGN PATENT DOCUMENTS

| CN | 101266204 A | 9/2008 |
| JP | 2008-136653 A | 6/2008 |
| WO | 99/20378 A1 | 4/1999 |
| WO | 2005/087287 A1 | 9/2005 |

OTHER PUBLICATIONS

English translation of abstract of CN 101096801 A (published Jan. 2, 2008).
English translation of abstract of JP 2008-136653 A (published Jun. 19, 2008).
English translation of abstract of CN 101266204 A (published Sep. 17, 2008).

* cited by examiner

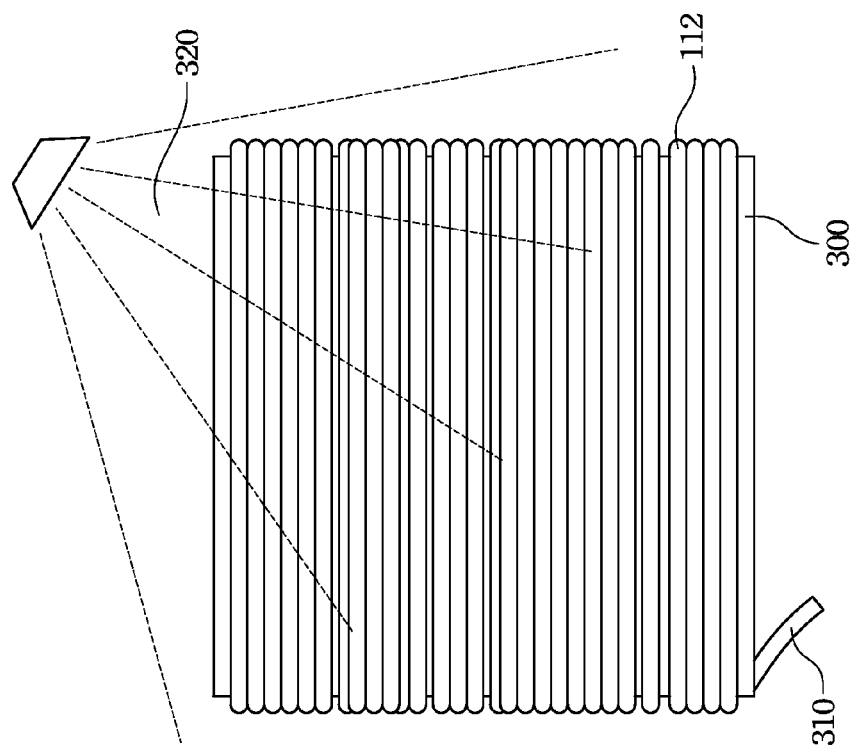
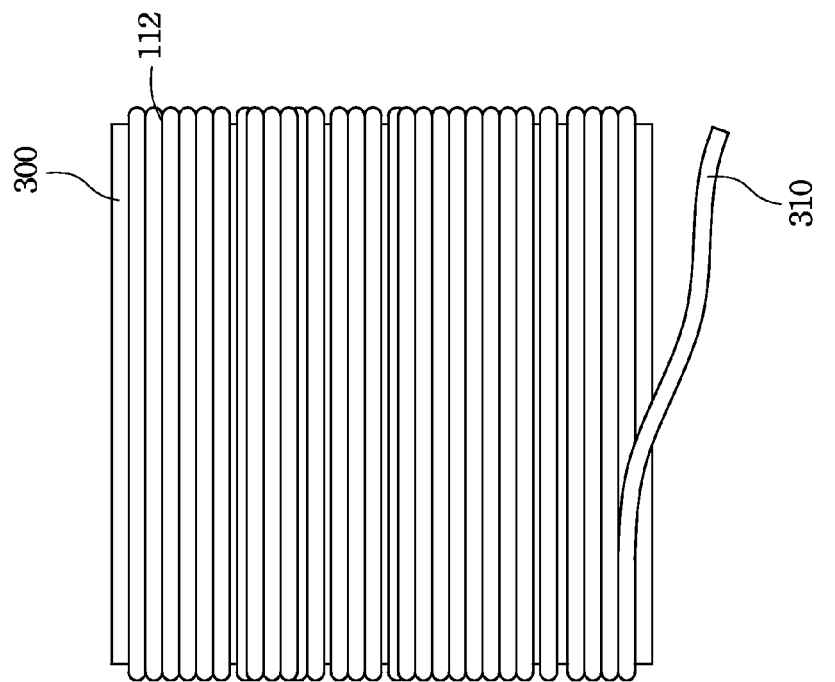
Fig. 3B
Fig. 3A

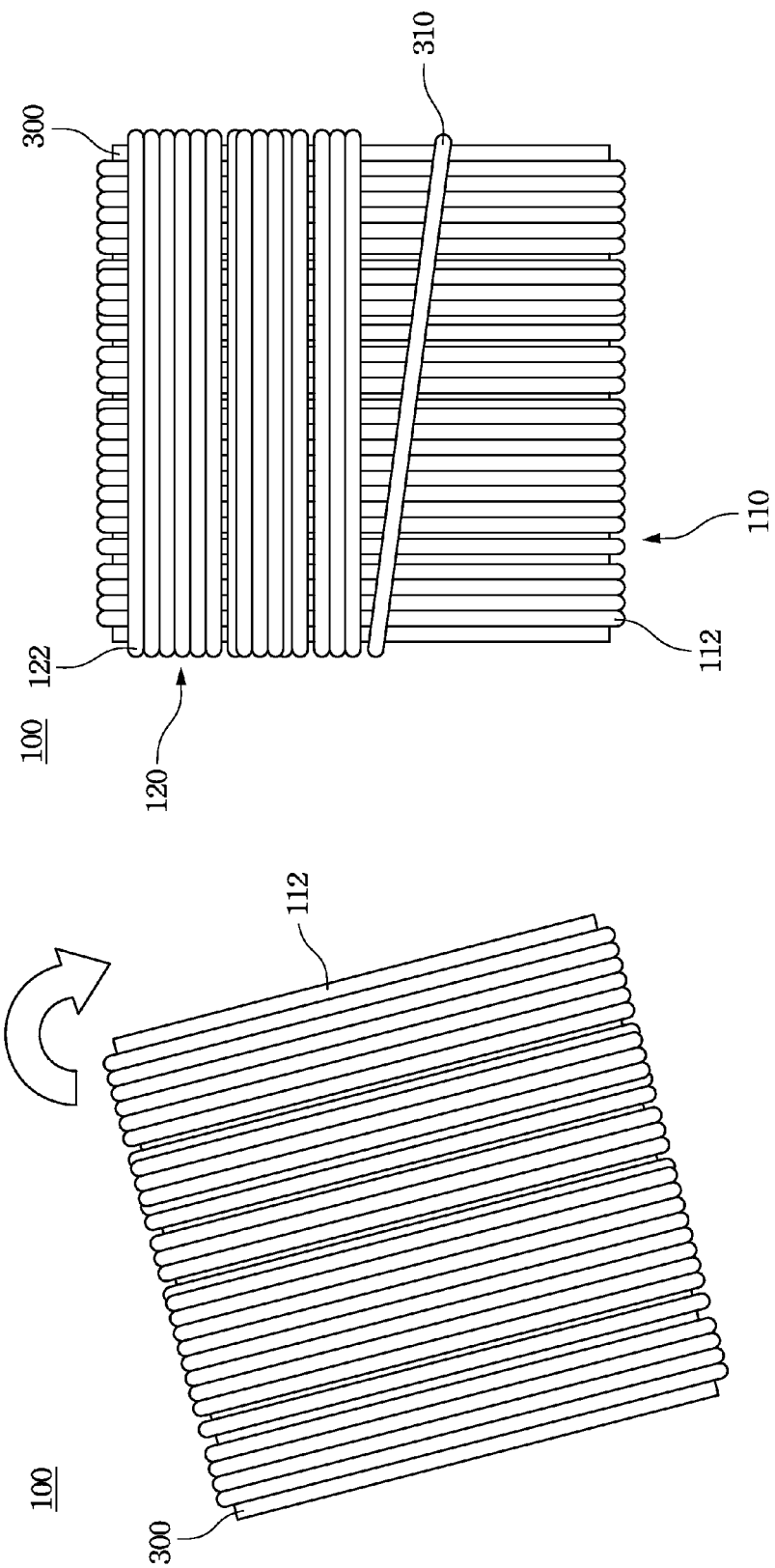

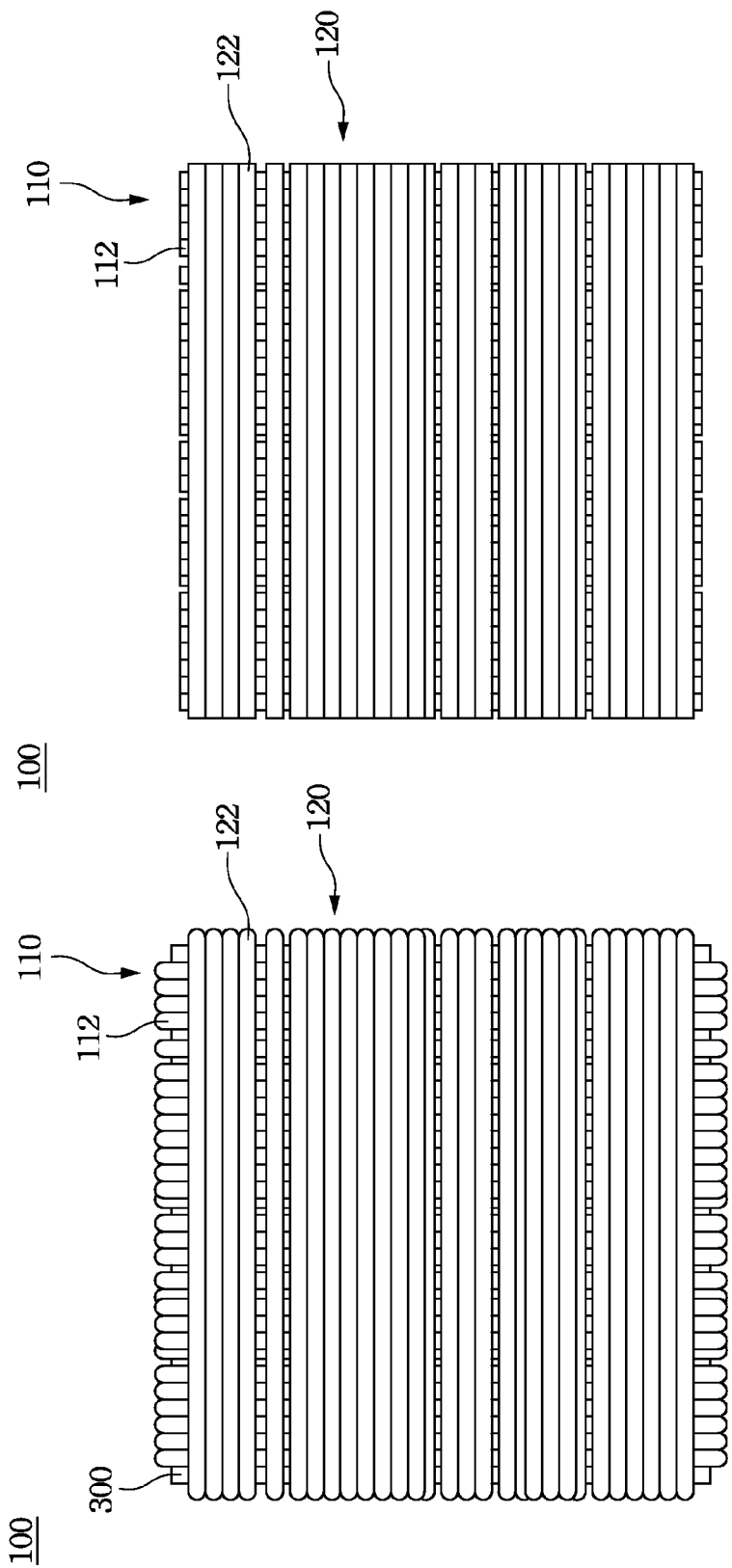

ALGINATE-CONTAINING WOUND DRESSING, METHOD AND APPARATUS FOR MAKING THE SAME

RELATED APPLICATIONS

The present application is a divisional of U.S. application Ser. No. 12/648,107, filed on Dec. 28, 2009, which claims priority to Taiwan application no. 98125403, filed Jul. 28, 2009. The entire disclosures of the above applications are hereby incorporated by reference herein.

BACKGROUND

1. Field of Invention

The present disclosure relates to a wound dressing; more particularly to an alginate wound dressing.

2. Description of Related Art

Generally, skin wounds should be kept relatively dry so as to facilitate the healing process of the wounds may. Hence, gauzes are conventionally used to keep the wounds sterile and dry. However, gauzes may sometimes adhere to the tissues or exudates of the wound. Such adhesion may result in a secondary damage to the tissues around the wound during the removal of the gauzes.

Recently, it is established that a moistening environment may facilitate the healing of the wounds. The fluids secreted by the wound may contain various growth factors that are advantageous to the wound healing. These findings lead to the development of sealing wound dressing such as polyurethane membranes, or wound dressings containing materials such as chitin/chitosan, collagen or alginate.

Main components of alginates or alginate compounds are algal polysaccharides extracted from natural algae. Commercially available alginate wound dressings may be in the form of non-woven fabrics, membranes and sponges. For example, wound dressing KALTOSTAT® provided by BritCair, UK is in the form of non-woven fabrics.

Nevertheless, several disadvantages may be associated with existing alginate wound dressing in the form of non-woven fabrics. For example, physiological saline is usually applied to the wound tissues to wash away the remaining gels and exudates during the wound dressing removal process. However, the non-woven fabrics may usually break upon the washing treatment. Besides, conventional non-woven fabrics of the wound dressing are often made of chopped fibers (staples), which tend to come off the non-woven fabrics and adhere to the wound tissues to form short piles that may slowdown the healing of the wounds.

In view of the foregoing, there exists in the related art a need for a novel alginate wound dressing.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure provides a novel alginate-containing wound dressing that may prevent the problems such as short piles and breakage encountered by conventional non-woven alginate-containing wound dressings. Due to the relatively low breaking strength, the wound dressing may break or adhere to the wound thereby causing the formation of short piles during the removal of the conventional alginate-containing wound dressing from the wound.

In view of the foregoing, in one aspect, the present invention is directed to a novel wound dressing comprising fibers made from alginates (also known as alginate filaments). According to the present disclosure, the breaking strength of the wound dressing may be improved by controlling the length and arrangement of the fibers.

According to one embodiment of the present invention, the wound dressing comprises two fiber layers. The first fiber layer consists of a plurality of a first fiber that are made of an alginate wherein the first fibers are respectively bound with one another, and are substantially extended in parallel along a first direction. The second fiber layer consists of a plurality of a second fiber that are made of an alginate, wherein the second fibers are respectively bound with one another, and extend in parallel along a second direction that is not parallel to the first direction. The second layer is stacked on the first layer with the second fibers being bound with the first fibers. The first fibers and the second fibers respectively have a length such that the wound dressing has a breaking strength for at least 1.5 kg.

In another aspect, the present invention is directed to a method for making alginate-containing wound dressings with improved breaking strength.

According to one embodiment of the present invention, the method comprises the steps as follows. First, at least one alginate fiber is formed by a wet spinning process. The alginate fiber thus obtained is wound around a board thereby forming a plurality of a first fiber on a surface of the board. In this step, the first fibers extend in parallel along a first direction. Thereafter, an aqueous solution containing sodium ions is sprayed on the surface of the wound first alginate fibers. Then, the alginate fiber is rewound around the board thereby forming a plurality of second fibers that are stacked on the first fibers, wherein the second fibers extend in parallel along a second direction that is not parallel to the first direction. The first fibers and the second fibers are dried so that the first fibers and the second fibers are respectively bound with one another.

In yet another aspect, the present invention is directed to an apparatus for making alginate-containing wound dressings.

According to one embodiment of the present invention, the apparatus comprises a base; a slot disposed on the base and having two ends; a tension compensator slidably connected to the slot and being operable to connect to at least one fiber; and a take-up device. The take-up device comprises a shaft that rotates upon being driven, wherein the shaft is aligned with a level between the two ends of the slot; and a board secured on the shaft for winding the fiber connected to the tension compensator.

Many of the attendant features will be more readily appreciated as the same becomes better understood by reference to the following detailed description considered in connection with the accompanying drawings.

BRIEF DESCRIPTION OF THE DRAWINGS

The present description will be better understood from the following detailed description read in light of the accompanying drawings, wherein:

FIG. 3A to FIG. 3F respectively illustrate a process for making wound dressing according to another embodiment of the present disclosure;

Figure 4:
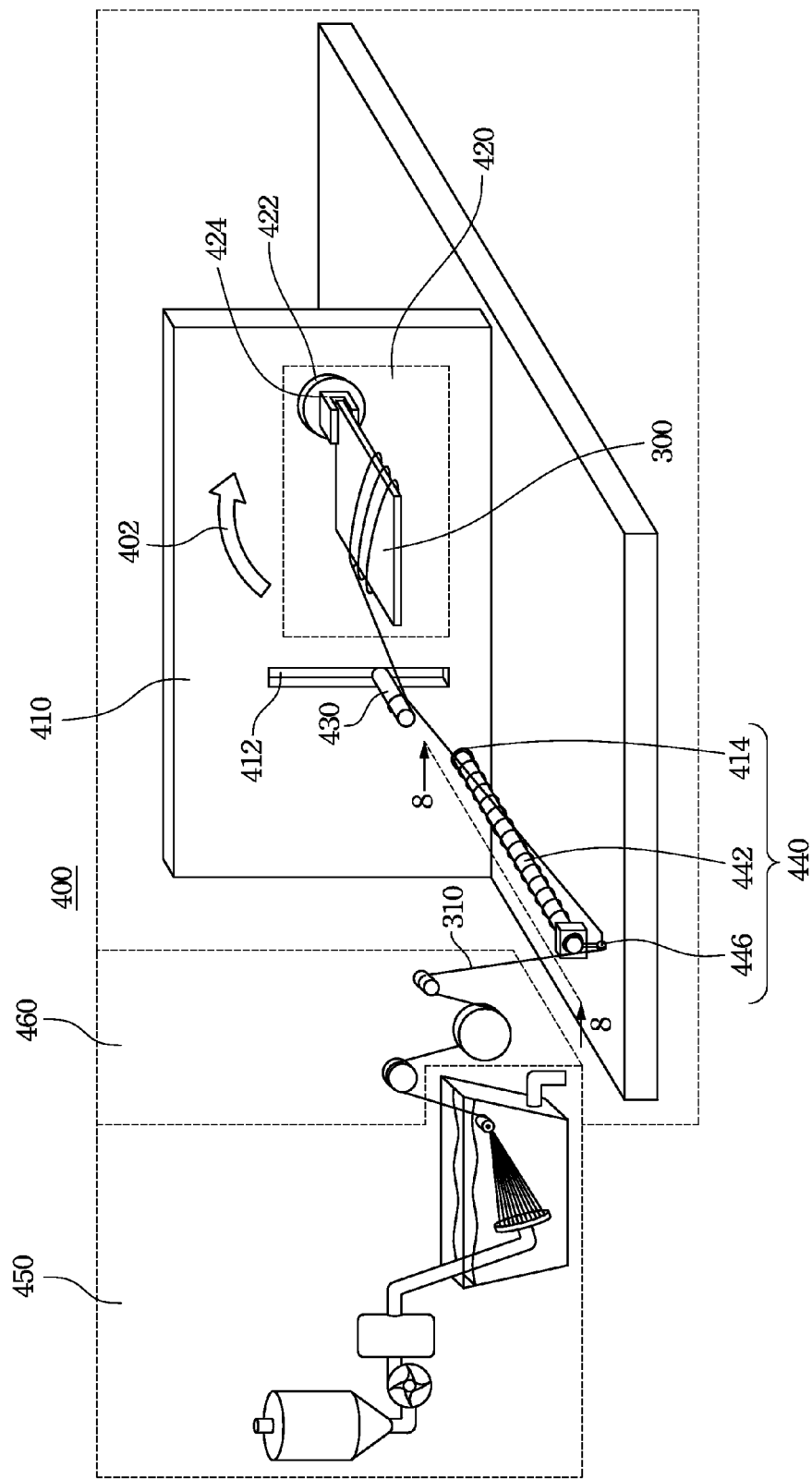
FIG. 4 is a front view illustrating an apparatus for making wound dressings according to one embodiment of the present disclosure.
Figure 6A:
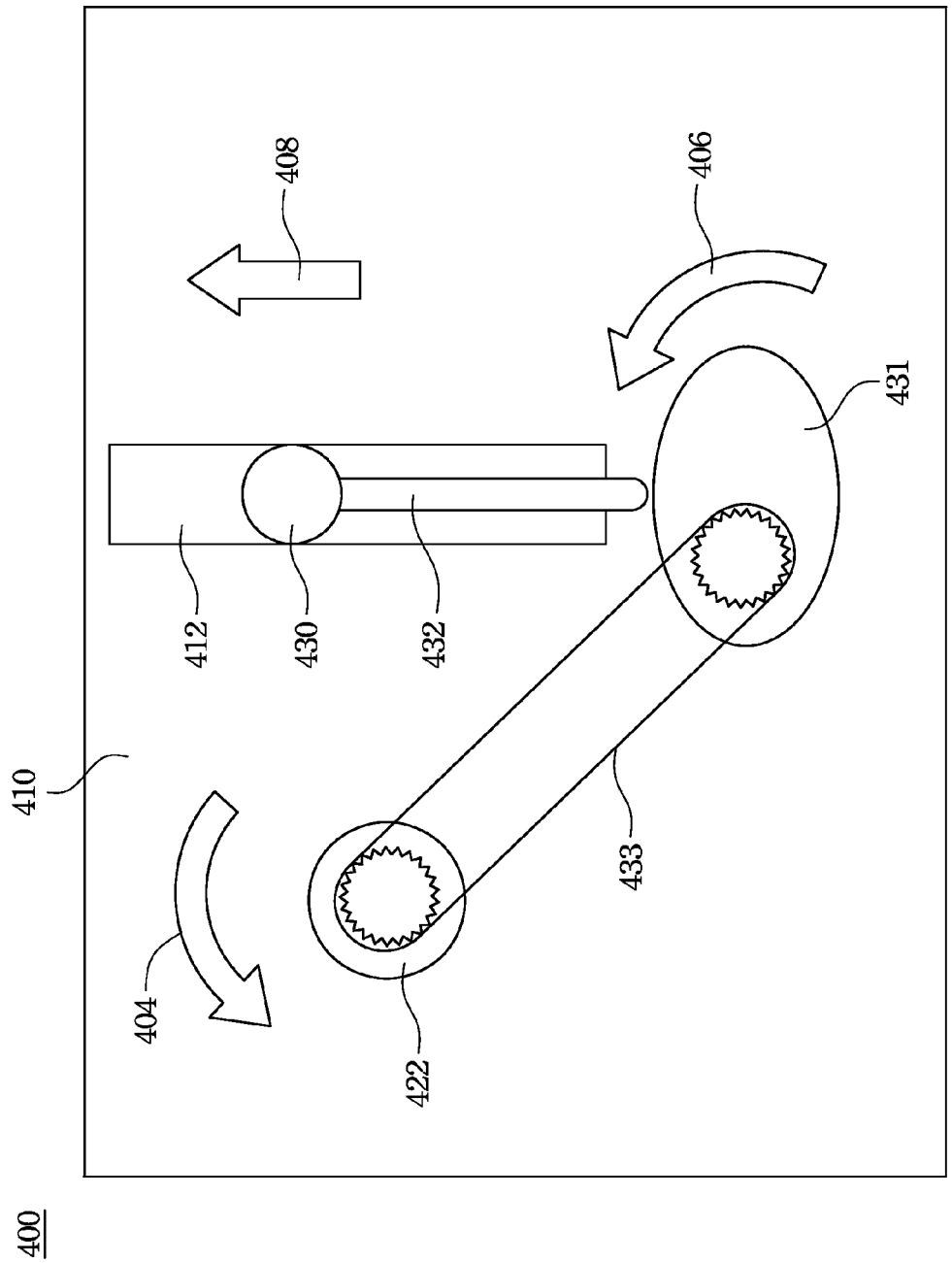
Figure 6B:
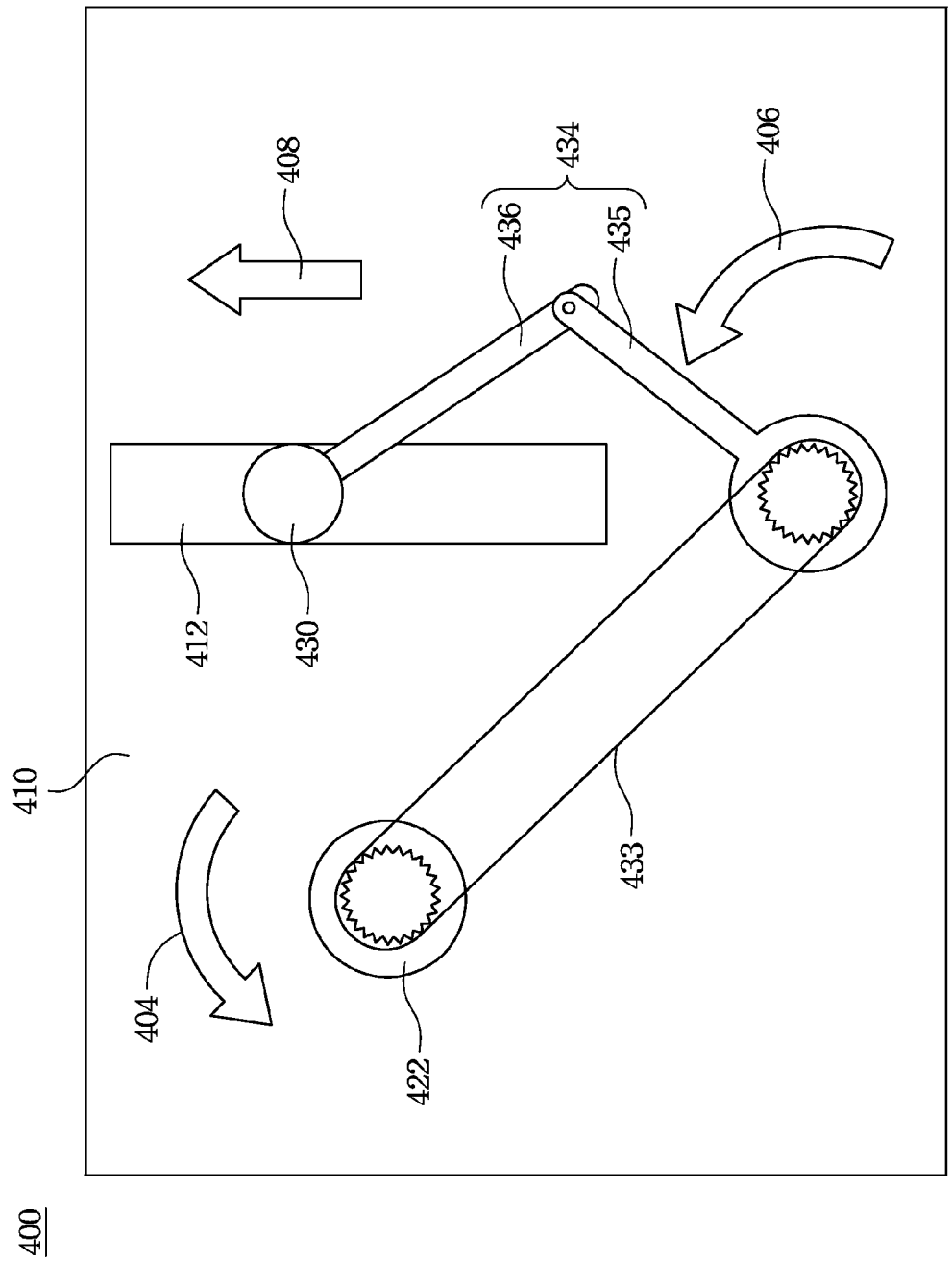
Figure 6C:
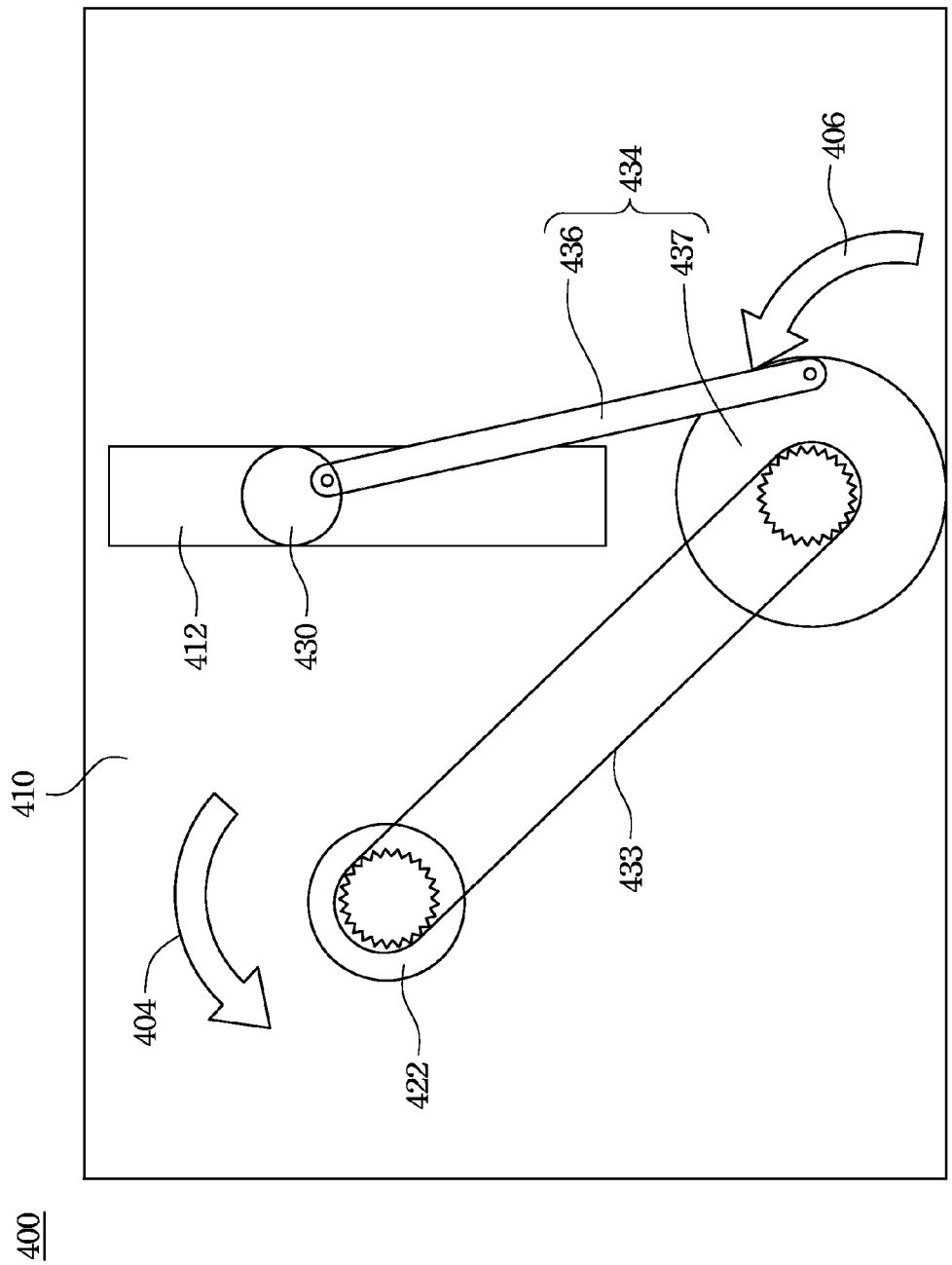
Figure 7:
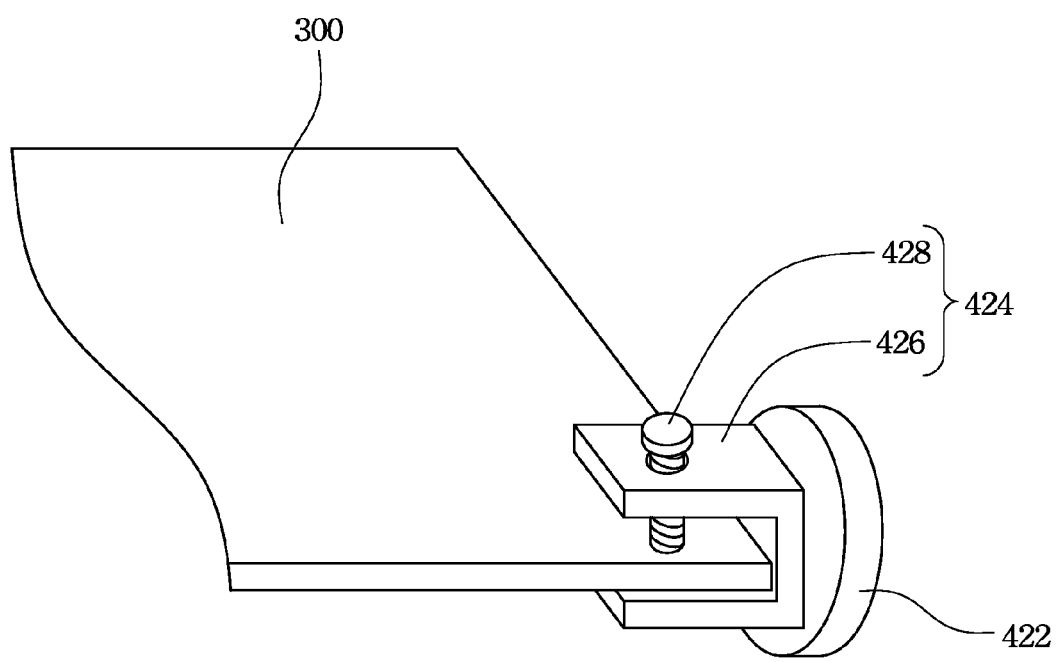
Figure 8A:
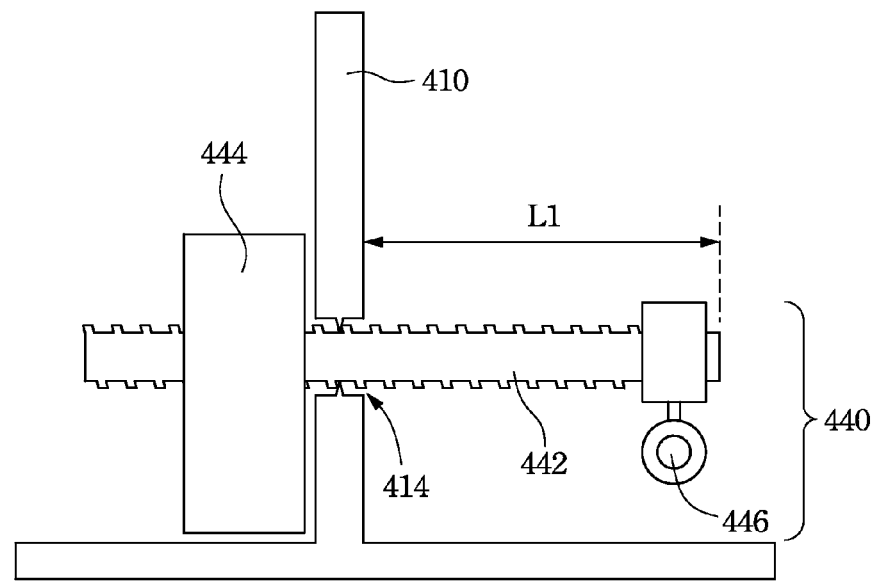
Figure 8B:
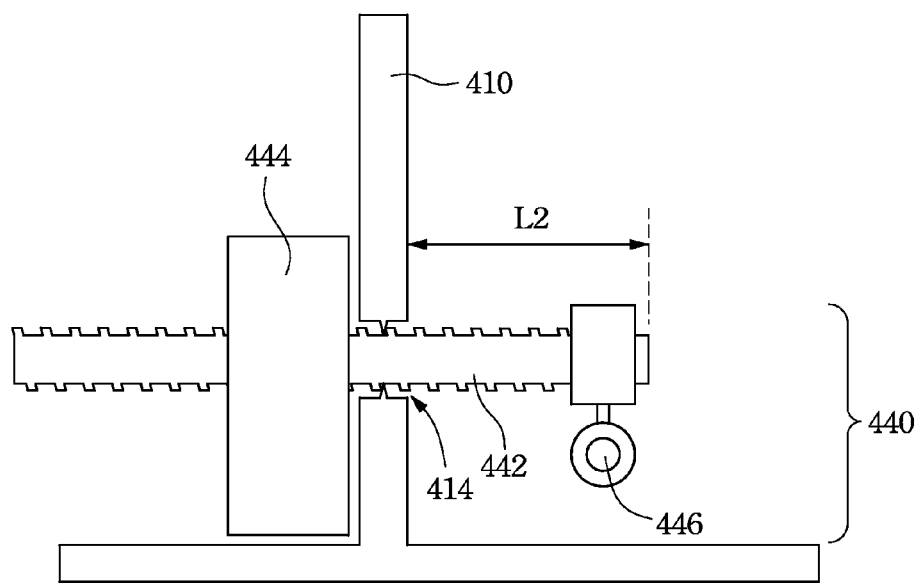

Each of FIG. 6A to FIG. 6C is a rear view illustrating an apparatus for making wound dressings according to various embodiments of the present disclosure;

FIG. 7 is a partially enlarged schematic diagram illustrating the apparatus of FIG. 4;

FIG. 8A and FIG. 8B are cross-sectional view taken along line 8 of FIG. 4 and each illustrates an operational status of the reciprocating device.

Like reference numerals are used to designate like parts in the accompanying drawings.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Figure 1A:
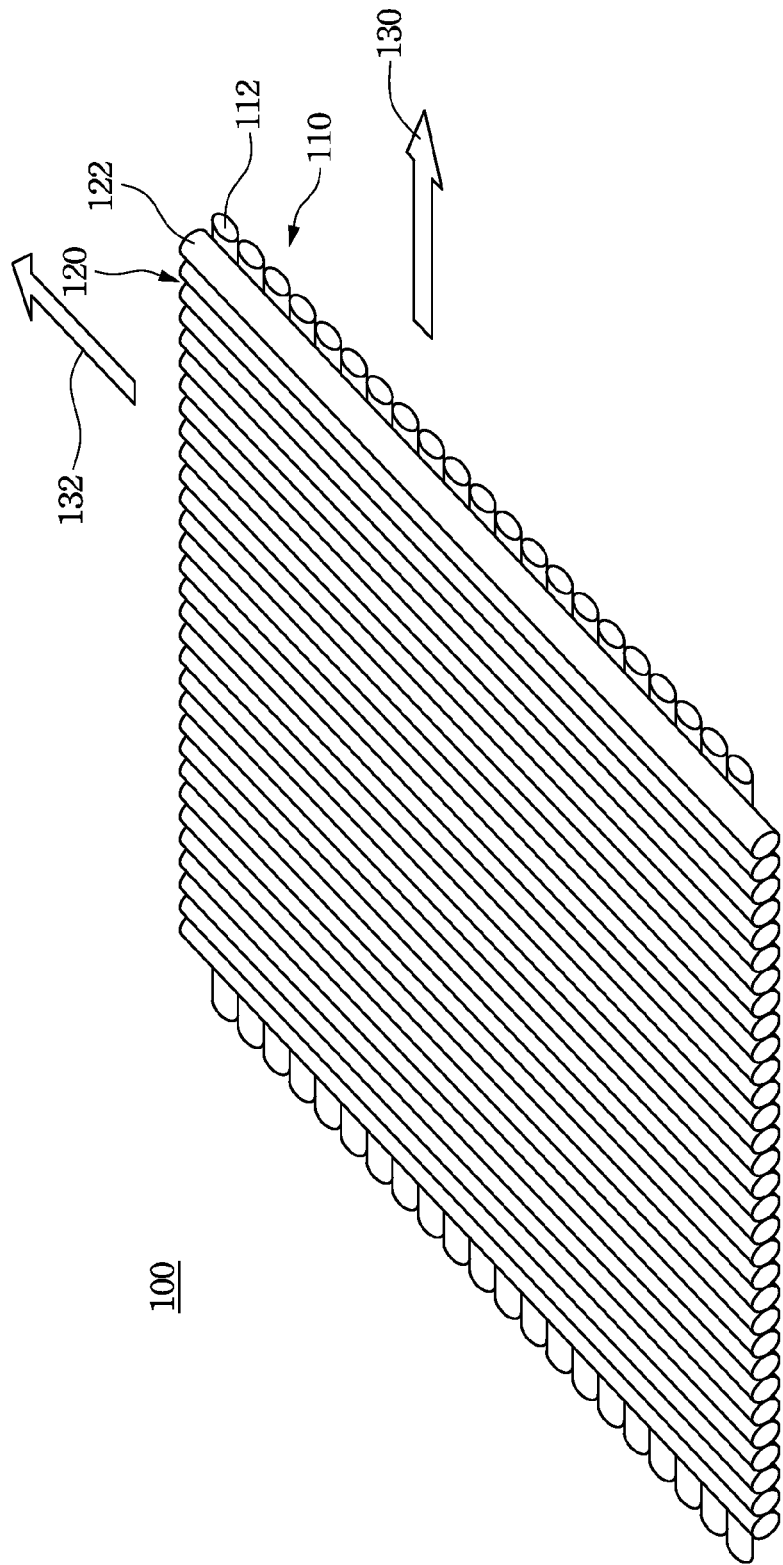
FIG. 1A is a schematic diagram illustrating the wound dressing according to one embodiment of the present disclosure.
Figure 1B:
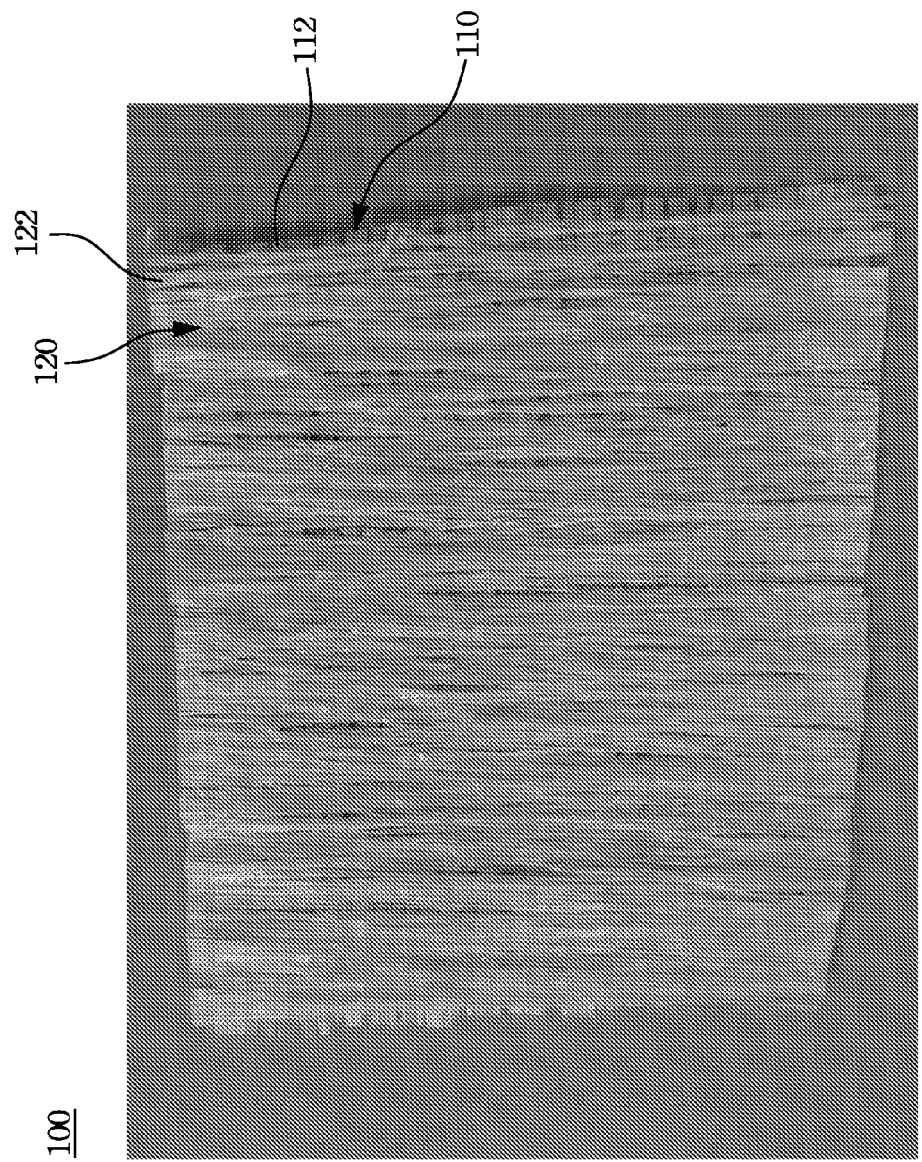
FIG. 1B is a photo of a wound dressing according to one embodiment of the present disclosure.

FIG. 1A is a schematic diagram illustrating the wound dressing 100 according to one embodiment of the present disclosure; whereas FIG. 1B is a photo of the wound dressing 100 according to one embodiment of the present disclosure.

Wound dressing 100 of the embodiment of the present disclosure mainly comprises fibers made from alginates. The breaking strength of the wound dressing 100 may be improved by controlling the length and arrangement of the fibers. Hence, problems such as short piles and breakage encountered by conventional non-woven alginate-containing wound dressings can be avoided.

In the present disclosure, the term "breaking strength" refers to the force applied on the wound dressing while the wound dressing breaks. In the working examples presented hereinafter, the breaking strength of the wound dressing is measured according to ASTM standard D 3822-2007 (Standard Test Method for Tensile properties of Single Textile Fibers).

The wound dressing 100 comprises two fiber layers—a first fiber layer 110 and a second fiber layer 120. Fibers of the two fiber layers are fibers with relatively long length. The breaking strength of the wound dressing 100 may be improved by designing the length and arrangement of the fibers of the first fiber layer 110 and the second fiber layer 120. Each element of the wound dressing 100 and characteristics thereof are set forth hereinafter.

The first fiber layer 110 consists of a plurality of a first fiber 112 that are made of an alginate wherein the first fibers 112 are respectively bound with one another. The first fibers 112 are substantially extended in parallel along a first direction, which is referred to as the first direction 130 hereinafter.

The second fiber layer 120 is stacked on first fiber layer 110. The second fiber layer 120 consists of a plurality of a second fiber 122 that are respectively bound with one another. The second fibers 122 are also made from alginate. The second fibers 122 are extend in parallel along a second direction, which is referred to as the second direction 132. The second direction 132 is not parallel to the first direction 130.

According to the embodiments of the present disclosure, the second fibers 122 are flatly disposed on and adhered to the first fibers 112 when the second fiber layer 120 is stacked on first fiber layer 110. In other words, the first fibers 112 and the second fibers 122 are solely adhered rather than woven with each other; that is, each of the first fibers 112 would not wind around each of the second fibers 122.

The first fibers 112 and second fibers 122 are all made from alginate, which is extracted from natural marine algae. Main components of the alginic acid molecule include β-D-mannuronic acid and α-L-guluronic acid that are irregularly arranged across the polymer chains. The polymer chains usually links with one another with the alternating β-D-mannuronic acid and α-L-guluronic acid or the polymeric alternating [β-D-mannuronic acid and α-L-guluronic acid] n. According to embodiment of the present disclosure, examples of alginate may include, but are not limited to, calcium alginate, barium alginate, copper alginate, zinc alginate, silver alginate or iron alginate.

According to the embodiments of the present disclosure, the first fibers 112 are bound with the second fibers 122 so as to improve the breaking strength of the wound dressing 100. During the manufacturing process, aqueous solution containing sodium ions can be sprayed onto the surfaced of the formed alginate fibers such as the first fibers 112 so that the surface of the fibers may be slightly dissolved or soften whereby producing viscose to bind any two adjacent first fibers 112. After the viscose is dried, the first fibers 112 are bound to one another. The second fibers 122 can be prepared by the above-mentioned method. Furthermore, the aqueous solution containing sodium ions may be sprayed on the surface of the first fiber layer 110; afterward, the second fiber layer 120 is stacked on the first fiber layer 110. As such, the first fibers 112 may adhere to the second fibers 122.

Aqueous solution containing sodium ions 320 may be a sodium chloride aqueous solution. The concentration of the sodium chloride in the aqueous solution may depend on the operation parameters. In one embodiment of the present disclosure, the sodium chloride is in an amount of about 1 wt % to about 15 wt %. For example, the concentration of the sodium chloride in the aqueous solution may be about 1, 2, 3, 4, 5, 6, 7, 8, 9, 10, 11, 12, 13, 14 or 15 wt %. In one working example presented hereinafter, the sodium chloride is in an amount of 10 wt %.

Conventional wound dressings made of non-woven fabric consists of alginate staples. The breaking strength of such conventional wound dressing is about 1.493 kgf. Such breaking strength is not sufficient to cope with the force applied during the removal of the wound dressing thereby causing problems such as wound dressing breakage and short piles formation. As such, according to the principles and spirits of the present disclosure, the first fibers 112 and the second fibers 122 should respectively have a sufficient length such that the wound dressing has a breaking strength for at least about 1.5 kgf.

According to embodiments of the present disclosure, the first fibers 112 and the second fibers 122 are both in a form of filaments. Each filament has a length no less than about 1 cm such that the breaking strength of the wound dressing is at least about 1.5 kgf.

It is well known that within a suitable range, the longer the fibers are, the higher the linear strength of the fiber. In the present disclosure, the linear strength represents the tensile of the fiber. Hence, the higher the linear strengths of the first fibers 112 and the second fibers 122 are, the higher the breaking strength of the wound dressing 100.

According to the embodiments of the present disclosure, breaking strengths of three samples were measured in accordance with the ASTM standard D 3822-2007. The lengths of the first fibers 112 and second fibers 122 of each of the samples were different from one another. The lengths of the fibers and test results are summarized in Table 1. As shown in Table 1, the lengths of the first fibers 112 and the second fibers 122 provide sufficient linear strength so that the breaking strength of the wound dressing 100 is in a range of about 107 kgf to about 109 kgf.

TABLE 1

| Length of the 1st fibers (cm) | Length of the 2nd fibers (cm) | Breaking strength (kgf) |
|---|---|---|
| 5 | 7 | 108.339 |
| 10 | 12 | 107.773 |
| 15 | 20 | 108.813 |

Hence, according to various embodiments of the present disclosure, each of the first fibers 112 and each the second fibers 122 may respectively have a sufficient length so that the breaking strength of the wound dressing is in a range of about 100-109 kgf. Specifically, the breaking strength may be about 100, 101, 102, 103, 104, 105, 106, 107, 108, or 109 kgf.

As can be concluded from the examples summarized in Table 1, each of the first fibers 112 and each of the second fibers 122 may have a respective length in the range of about 5-20 cm so as to achieve the breaking strength specified above. In particular, the length of the each of the first and second fibers can be 5, 6, 7, 8, 9, 10, 11, 12, 13, 14, 15, 16, 17, 18, 19, or 20 cm.

Furthermore, in the examples shown in Table 1, the length of the first fibers 112 is equal to or slightly smaller than the width of the wound dressing 100, and the length of the second fibers 122 is also equal to or slightly smaller than the length of the wound dressing 100. Such arrangement is also suitable in other embodiments of the present disclosure.

The first fibers 112 extend in a direction parallel to the first direction 130, whereas the second fibers 122 extend in a direction parallel to the second direction 132 that is not parallel to the first direction 130. In other words, there is an included angle between the first direction 130 and the second direction 132, wherein the included angle is in a range between about 0° to 180°, both ends excluded. The included angle may be, for example, about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees. According to one optional embodiment of the present disclosure, the first direction 130 is substantially perpendicular to the second direction 132.

Therefore, in the wound dressing 100, the breaking strength in each direction can be improved by selecting suitable lengths and extending directions of the first fibers 112 and second fibers 122. In particular the breaking strength in the directions of the first direction 130 and second direction 132 may be improved.

It should be noted that although wound dressing 100 having two fiber layers are illustrated in the above embodiments, the wound dressing 100 may have more than two fiber layers, such as three, four, five or more fiber layers. In the latter case, the extension direction of fibers in each of the fiber layers may be non-parallel to the extension directions of fibers in other fiber layers.

Figure 2:
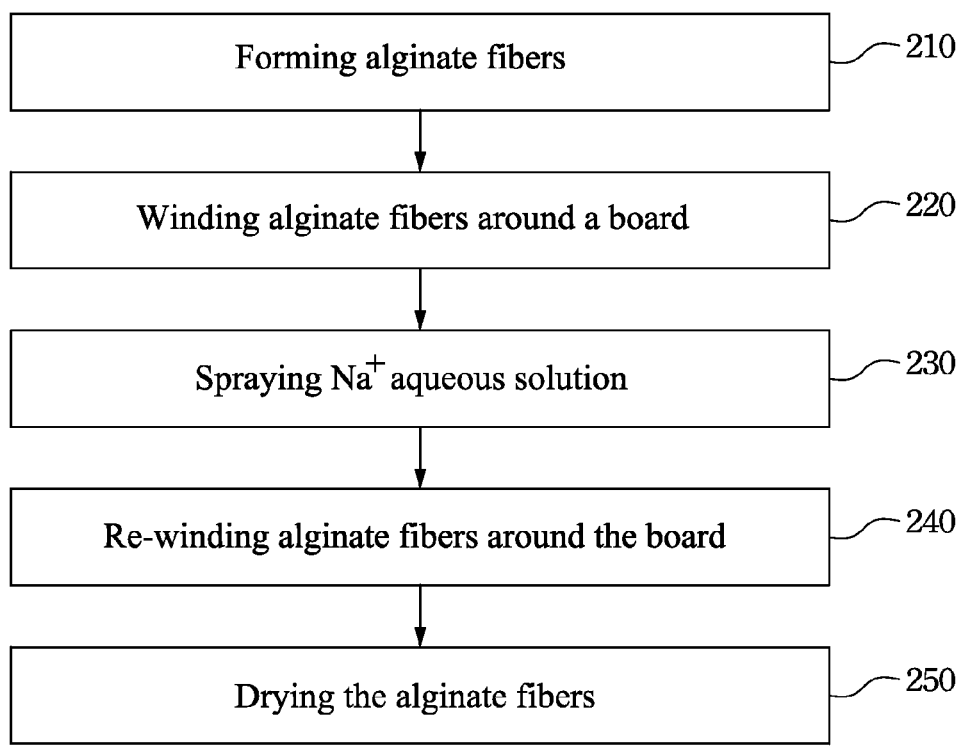
FIG. 2 is a flow chart illustrating the method for making a wound dressing according to one embodiment of the present disclosure.

FIG. 2 is a flow chart illustrating the method 200 for making the wound dressing 100 according to one embodiment of the present disclosure. FIG. 3A to FIG. 3F are schematic diagrams illustrating the process steps for making the wound dressing 100 according to one embodiment of the present disclosure.

Please refer to FIG. 2 and FIG. 3A. The first step 210 of the method 200 for making the wound dressing 100 is forming alginate fibers. In step 210, at least one alginate fiber 310 can be formed by a wet spinning process. Specifically, the wet spinning process comprises the steps as follows. Alginate compounds are dissolved in an aqueous solution to form a spinning solution. From a spinning nozzle, the spinning solution is injected into a molding basin containing divalent metal ions ($M^{2+}$) so that the spinning solution is injection molded into a solid, insoluble alginate fiber 310. According to the embodiments of the present disclosure, the alginate compounds may be calcium alginate, barium alginate, copper alginate, zinc alginate, silver alginate or iron alginate.

Alternatively, after the alginate fiber 310 is formed, the alginate fiber 310 can be extended by a drafting process so as to adjust the linear strength of the alginate fiber 310. The drafting process can be performed by a drafting roller assembly. The structure of the drafting roller and the method for drafting the fibers are known to those skilled in the art, and hence are not described in detailed in the present disclosure.

In step 220, the alginate fiber 310 is wound around a board 300. After winding, the alginate fiber 310 would be arranged in parallel on a surface of the board 300 as a plurality of fragments. In the present disclosure, one fragment of the alginate fiber 310 disposed on a surface of the board 300 is referred to as a first fiber 112. The length of the first fibers 112 is equal to or slightly smaller than the length of the board 300. According to the embodiments of the present disclosure, the length of each of the first fibers 112 is in a range of about 5 cm to about 20 cm. Specifically, the length can be about 5, 6, 7, 8, 9, 10, 11, 12, 13, 14, 15, 16, 17, 18, 19, or 20 cm.

Please refer to FIG. 2 and FIG. 3B. Step 230 is carried out after the winding the alginate fiber 310. In step 230, an aqueous solution containing sodium ions 320 is sprayed on the surface of the wound alginate fiber 310. Spraying the aqueous solution containing sodium ions 320 over the surface of the solidified alginate fiber 310 may slightly dissolve or soften the surface of the alginate fiber 310 whereby producing viscose. The adjacent fragments of the alginate fiber 310 (i.e., first fibers 112) would be adhered together by the viscose. After the viscose is dried, the adjacent fragments would bind with one another.

The aqueous solution containing sodium ions 320 may be a sodium chloride aqueous solution. The concentration of the sodium chloride in the aqueous solution may depend on the operation parameters. In one embodiment of the present disclosure, the sodium chloride is in an amount of about 1 wt % to about 15 wt %. For example, the concentration of the sodium chloride in the aqueous solution may be about 1, 2, 3, 4, 5, 6, 7, 8, 9, 10, 11, 12, 13, 14 or 15 wt %. In one working example presented hereinafter, the sodium chloride is in an amount of 10 wt %.

Please refer to FIG. 2, FIG. 3C and FIG. 3D. After the first winding step is accomplished, the board 300 is rotated as shown in FIG. 3C. Afterward, in step 240, the alginate fiber 310 is re-wound around the board 300 as shown in FIG. 3D. After this re-winding step, the alginate fiber 310 would be arranged in parallel on a surface of the board 300 as a plurality of fragments, which are referred to as second fibers 122. The length of the second fiber 122 is equal to or slightly smaller than the length of the board 300. According to the embodiments of the present disclosure, the length of each of the second fibers 122 is in a range of about 5 cm to about 20 cm. Specifically, the length can be about 5, 6, 7, 8, 9, 10, 11, 12, 13, 14, 15, 16, 17, 18, 19, or 20 cm The second fibers 122 are stacked on the first fibers formed on the board 300 during the first winding step (step 220). It should be noted that the board 300 is rotated between the first (step 220) and second (step 240) winding steps such that the extension direction of the first fibers 112 is different from that of the second fibers 122. In other words, the rotation angle of the board 300 is equal to the included angle between the extension directions of the first fibers 112 and the second fibers 122. For the purpose of illustration, the board 300 can be rotated with an angle in the range of about 0-180 degrees, both ends excluded. For example, the rotation angle can be about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, or 175 degrees. According to one optional embodiment of the present disclosure, the board 300 is rotated at an angle of about 90 degrees.

Please refer to FIG. 2, FIG. 3E and FIG. 3F. After the re-winding step, the wound dressing 100 can be obtained by cutting the fibers along the peripheral of the board 300, as shown in FIG. 3F.

Afterward, step 250 is carried out to dry the alginate fibers. As illustrated hereinabove, spraying the aqueous solution containing sodium ions 320 on the surface of the solidified alginate fibers 310 would cause the formation of viscose. After the viscose is dried, the adjacent alginate fibers 310 would be bound with one another.

According to the embodiments of the present disclosure, the alginate fibers 310 may be dried by freeze-drying. The freeze-drying technique can be embodied in various method, and the temperature and pressure used in the freeze-drying process may be process-dependent. According to embodiments of the present disclosure, the temperature for the freeze-drying is about −55° C. to about −20° C., and the pressure is about 12 pascals.

It should be noted that although steps of the method according to embodiments of the present disclosure are recited in a specific sequence, the method is not limited thereto. That is, unless the sequence of the steps is expressly indicated, the sequence of the steps is interchangeable, and all or part of the steps may be simultaneously, partially simultaneously, or sequentially performed. In addition, each step may be performed more than once. For example, the step of spraying the aqueous solution containing sodium ions 320 and the step of winding alginate fibers 310 can be performed more than once.

Besides, the step of spraying the aqueous solution containing sodium ions is not limited to be performed after the first winding step (step 220). In fact, the spraying step can be performed simultaneously with and/or after the first winding step (step 220) and/or the re-winding step (step 240).

FIG. 4 is a front view illustrating an apparatus 400 for making wound dressings 100 according to one embodiment of the present disclosure. The apparatus 400 comprises a base 410, a take-up device 420 and a tension compensator 430. The take-up device 420 is operable to wind the alginate fiber 310. The take-up device 420 may comprises a shaft 422 and a board 300, wherein the board 300 is secured on the shaft 422. When the shaft 422 is rotated (for example, rotated along direction 402 shown in FIG. 4) upon driven, the alginate fiber 310 would be wound around the board 300.

The shape of the board 300 is different from that of the conventional cylindrical beaming. As such, during the take-up process, the length of the alginate fiber 310 may be altered in an excess level thereby altering the tension of the alginate fiber 310. To address such problem, a tension compensator 430 is disposed in front of the take-up device 420 so as to maintain the tension of the alginate fiber 310 during the take-up process.

Specifically, a slot 412 is disposed on the base 410 and is adjacent to the shaft 422. The slot 412 has two ends defining a lengthwise direction. The shaft 422 is disposed at a place so that the shaft 422 is aligned with a level between the two ends of the slot 412. The tension compensator 430 is disposed in the slot 412 and operable to slide in the lengthwise direction of the slot 412.

Figure 5A:
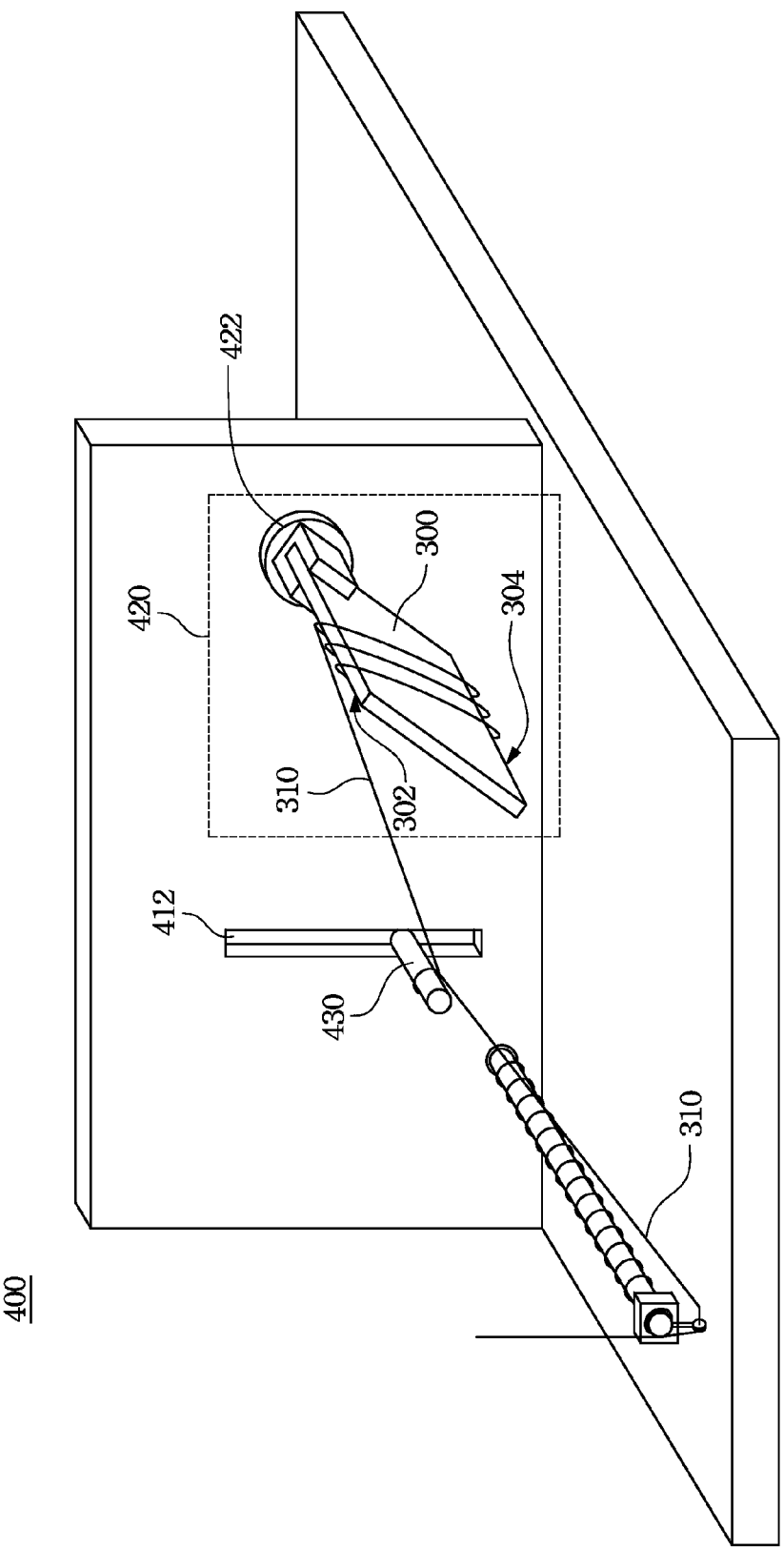
FIG. 5A and FIG. 5B respectively illustrate the various operational status of the apparatus of FIG. 4.
Figure 5B:
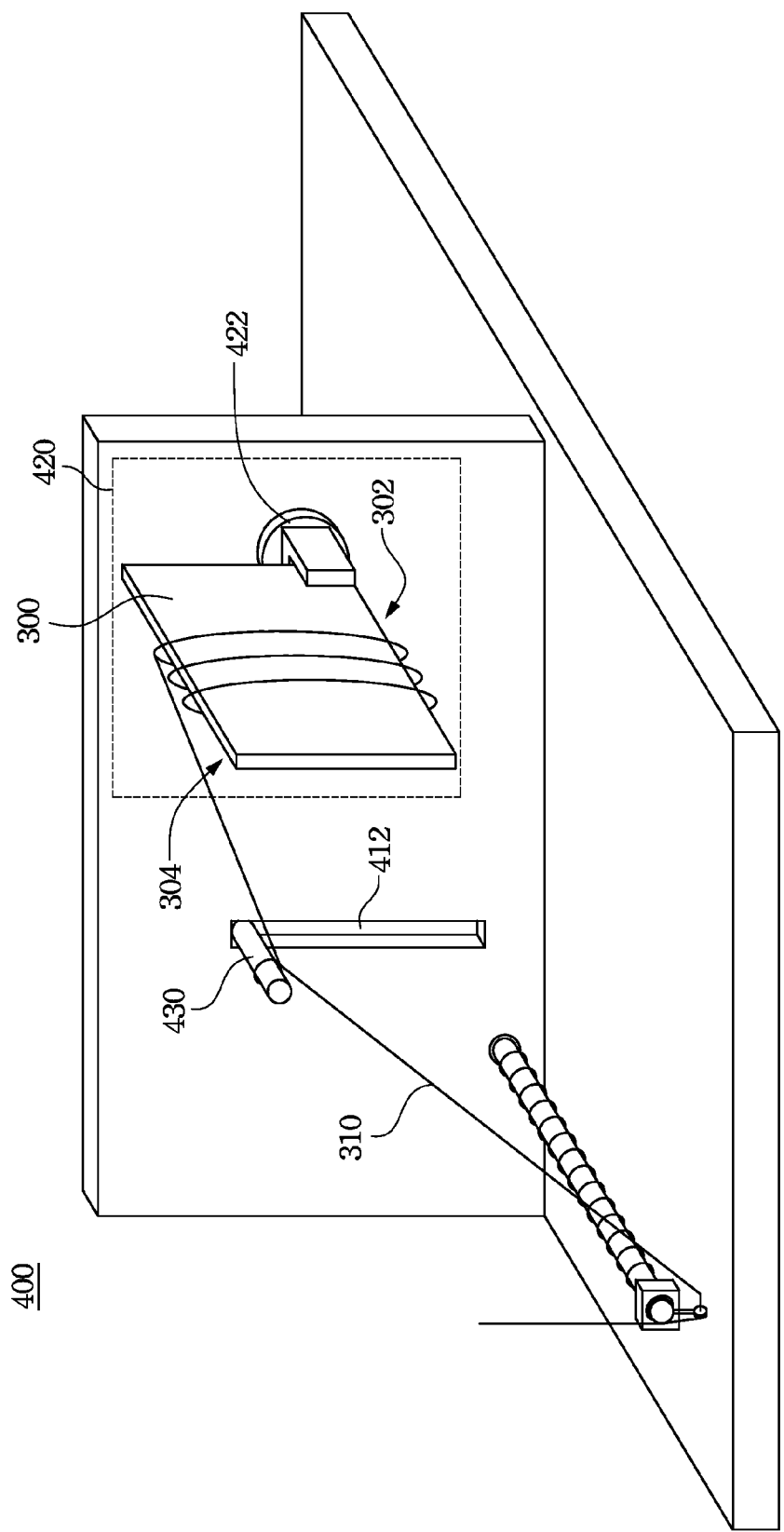

The tension compensator 430 is operable to connect to the alginate fiber 310. The tension compensator 430 may adjust the tension of the alginate fiber 310 by altering its altitudinal position in the slot 412. Please refer to FIG. 5A and FIG. 5B, which respectively illustrates the various operational status of the apparatus 400 of FIG. 4. When an edge 304 of the board 300 is rotated to a position lower than the altitude of the shaft 422, the tension compensator 430 may slide to a lower altitudinal position in the slot 412. For example, the tension compensator 430 may slide to a position lower than the shaft 422, as shown in FIG. 5A. On the other hand, when the edge 304 of the board 300 is rotated to a position higher than the altitude of the shaft 422, the tension compensator 430 may slide to a higher altitudinal position in the slot 412. For example, the tension compensator 430 may slide to a position higher than the shaft 422, as shown in FIG. 5B.

As such, the length variation of the alginate fiber 310 between the tension compensator 430 and the edges 302 or 304 can be decreased thereby maintaining a stable tension of the alginate fiber 310.

It should be noted that the length of the slot 412 is not limited in the embodiments of the present disclosure. For example, when one of the edges 302 or 304 of the board 300 is rotated to the highest position, said highest position may be higher or lower the upper end of the slot 412. When one of the edges 302 or 304 of the board 300 is rotated to the lowest position, said lowest position may be higher or lower the lower end of the slot 412. In one embodiment, when the edge 304 of the board 300 is rotated to the highest position, the upper end of the slot 412 is substantially aligned with the middle of the edge 304 and the shaft 422. When the edge 304 of the board 300 is rotated to the lowest position, the lower end of the slot 412 is substantially aligned with the middle of the edge 304 and the shaft 422.

According to the embodiments of the present disclosure, the length of the slot 412 may be smaller than one-fold or two-fold the distance between the shaft 422 and the edge 304 of the board 300.

Tension compensator 430 may be reciprocatively slide in the lengthwise direction of the slot 412 under the pulling motion of the alginate fiber 310. That is, when the alginate fiber 310 is rotated to a position higher than the shaft 422 under the rotating motion of the board 300, the alginate fiber 310 may pull the tension compensator 430 to slide upward. On the contrary, when the alginate fiber 310 is rotated to a position lower than the shaft 422 under the rotating motion of the board 300, the alginate fiber 310 may pull the tension compensator 430 to slide downward.

Alternatively, the tension compensator 430 may couple with the shaft 422 by means of gear, screw, strap, cam, link lever or other mechanical members. Hence, the tension compensator 430 may slide along the lengthwise direction of the slot 412 under the driving force provided by the shaft 422.

FIG. 6A is an illustrative example illustrating the rear view of the apparatus 400 according to embodiments of the present disclosure. As shown in FIG. 6A, apparatus 400 comprises cam 431, rod 432 and a banded structure 433 such as a strap. The shaft 422 and cam 431 are connected by the banded structure 433. On end of the rod 432 connects to the tension compensator 430, whereas the other end of the rod 432 is against the cam 431. When the shaft 422 is driven to rotate in the direction 404, the cam 431 would be driven to rotate in the direction 406 through the action of the banded structure 433. The cam 431 and rod 432 are disposed in a way such that the cam 431 would push the rod 432 and the tension compensator 430 to slide in the lengthwise direction of the slot 412.

Another example of apparatus 400 is illustrated in FIG. 6B. The tension compensator 430 is driven by the shaft 422 through the action of the link lever 434. In particular, the linkage 434 may comprise a mechanism such as crank 435 and a rocking lever 436. The shaft 422 and the crank 435 are connected by a banded structure 433 such as a strap. One end of the rocking lever connects to the tension compensator 430, whereas the other end connects to the crank 435. When the shaft 422 is rotated in the direction 404, the crank 435 is rotated through the action of the banded structure 433 which in turns may drive the rocking lever 436 to rock so that the tension compensator 430 may reciprocally slide in the lengthwise direction of the slot 412.

Still another example of the apparatus 400 is illustrated in FIG. 6C. The tension compensator 430 is driven by the shaft 422 through the linkage 434. Specifically, linkage 434 may comprise a wheel 437 and a rocking lever 436. Two ends of the rocking lever 436 pivotally connect to the wheel 437 in the proximity of the periphery of the wheel 437 and the tension compensator 430, respectively. The shaft 422 and the wheel 437 are connected by the banded structure 433 such as a strap 433. When the shaft 422 is rotated in direction 404, the wheel 437 would rotate in the direction 406 under the action of the banded structure 433 which in turns would drive the rocking lever 436 to rock, thereby driving the tension compensator 430 to reciprocally slide in the lengthwise direction of the slot 412.

In the above-described examples, a banded structure is used to connect the members. Alternatively, the banded structure 433 can be replaced by a gear set for connecting the shaft 422 and the tension compensator 430.

It is apparent from the examples described above that the tension compensator 430 can be connected to the shaft 422 by means of a cam 431, a linkage 434 and any other suitable mechanical members so that the tension compensator 430 may move synchronically with the rotation of the shaft 422.

Alternatively, an automated control module can be employed. The automated control module may electrically connect to the shaft 422 so as to detect the rotation of the shaft 422 and adjusting the altitudinal position of the tension compensator 430 based on the result of the detection.

The board 300 is detachable; that is, the board 300 can be secured on and detached from the shaft 422. The apparatus 400 may comprises a clamp 424 fixed on the shaft 422. The clamp 424 is operable to secure or release the board 300. As such, during two winding processes, the board 300 can be released, rotated, and then re-secured on the shaft 422.

Examples of clamp 424 for securing the board 300 on the shaft 422 may include, but are not limited to: elastic clamps, C-clamps and combinations thereof. Please refer to FIG. 7, which is a partially enlarged schematic diagram illustrating the apparatus 400 according to one embodiment of the present disclosure. According to the embodiments of the present disclosure, clamp 424 may comprises a clamping seat 426 and a screw 428. The clamping seat 426 is fixed on the shaft 422 and is used for accommodating a portion of the board 300 therein. The screw 428 is secured into the clamping seat 426 whereby securing the board 300 in the clamping seat 426. The board 300 can be detached from the clamping seat 426 by releasing the screw 428.

To avoid the adherence between the alginate fiber 310 and the board 300, the board 300 should be made of a material that would not react with the alginate compound, and should have a smooth surface. According to the embodiments of the present disclosure, the material of the board 300 can be acrylic resins. The shape of the board 300 may depends on the desired shape of the product. For example, the shape of the board 300 can be square, rectangle, rhombus, polygonal or circle.

Please refer to FIG. 4. The apparatus 400 may comprise a reciprocating device 440 disposed in front of the take-up device 420. The reciprocating device 440 is operable to drive the alginate fiber 310 to reciprocatively move in a direction parallel to an axis of the shaft 422. As such, the alginate fibers 310 may evenly be distributed on the board 300 during the winding process.

Please refer to FIG. 4, FIG. 8A and FIG. 8B. FIG. 8A and FIG. 8B are cross-sectional view taken along line 8 of FIG. 4 and each illustrates an operational status of the reciprocating device 440.

The reciprocating device 440 comprises a rod 442 and an actuator 444. The rod 442 passes through a through-hole 414 on the base 410 and connects to the actuator 444. The actuator 444 is operable to push the rod 442 so that the rod may reciprocatively move in its extension direction thereby altering the distance between one end of the rod 442 and the through-hole 414. For example, the distance L1 between one end of the rod 442a to the through-hole (as shown in FIG. 6A) is altered to distance L2 (as shown in FIG. 6B).

In one embodiment of the present disclosure, the rod 442 is threaded, wherein the thread of the rod 442 is matched with the thread of the through-hole 414. The actuator 444 is operable to rotate the rod 442 so that the rod 442 may reciprocatively move in its extension direction. Alternatively, the actuator 444 may be a linear actuator which may push the rod 442 to reciprocatively move in its extension direction.

The reciprocating device 440 may further comprises a threaded hole 446 disposed at one end of the rod 442. The alginate fiber 300 may pass through the threaded hole 446. It should be noted that the threaded hole 446 would not rotate no matter whether or not the rod 442 is in a rotating motion.

It should be noted that various structures can be used to drive the alginate fiber 310 to move reciprocatively. Hence, examples provided herein are merely for the purpose of illustration, and the examples should not be regarded as limiting to the scope of the present disclosure.

According to the embodiments of the present disclosure, apparatus 400 may comprises a wet spinning module 450 for performing a wet spinning process to produce the alginate fiber 310. Detailed process for performing the wet spinning process is described hereinabove, and hence is not repeated here.

To improve the tension of the alginate fiber 310, the apparatus may further comprise a drafting roller module 460. The drafting roller module 460 is used for drafting the alginate fiber 310 so as to adjust the linear strength of the alginate fiber 310.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for manufacturing a wound dressing, comprising:
    forming at least one alginate fiber by a wet spinning process;
    winding the alginate fiber around a board thereby forming a plurality of first fibers on a surface of the board, wherein the first fibers extend in parallel along a first direction;
    spraying an aqueous solution containing sodium ions on the surface of the wound first alginate fibers;
    rewinding the alginate fiber around the board thereby forming a plurality of second fibers that are stacked on the first fibers, wherein the second fibers extend in parallel along a second direction that is not parallel to the first direction so that an included angle between the first direction and the second direction is in a range between about 0° to 180°; and
    drying the first fibers and the second fibers so that the first fibers and the second fibers are respectively bound with one another.

2. The method of claim 1, wherein the aqueous solution containing sodium ions comprises sodium chloride in an amount of about 1% to about 15%.

3. The method of claim 1, wherein the alginate is any of a calcium alginate, a barium alginate, a copper alginate, a zinc alginate, a silver alginate or an iron alginate.

4. The method of claim 1, further comprising:
    rotating the board with an angle that is equal to the included angle, before the rewinding step.

5. The method of claim 1, further comprising:
    drafting the alginate fibers by at least one drafting roller to adjust the breaking strength of the alginate fibers, after the wet spinning process.

* * * * *